US006646162B2

(12) United States Patent
Tang et al.

(10) Patent No.: US 6,646,162 B2
(45) Date of Patent: Nov. 11, 2003

(54) COMPOUNDS AND COMPOSITIONS FOR DELIVERING ACTIVE AGENTS

(75) Inventors: Pingwah Tang, Elmsford, NY (US); Andrea Leone-Bay, Ridgefield, CT (US); David Gschneidner, Stamford, CT (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 09/939,511

(22) Filed: Aug. 24, 2001

(65) Prior Publication Data

US 2002/0040061 A1 Apr. 4, 2002

Related U.S. Application Data

(63) Continuation of application No. PCT/US00/04830, filed on Feb. 25, 2000.
(60) Provisional application No. 60/121,850, filed on Feb. 26, 1999.

(51) Int. Cl.⁷ .............................................. C07C 233/00
(52) U.S. Cl. ................... 564/167; 548/543; 548/346.1; 544/222
(58) Field of Search .......................... 564/167; 548/543, 548/346.1; 544/222

(56) References Cited

U.S. PATENT DOCUMENTS

| | | | |
|---|---|---|---|
| 3,940,490 A | 2/1976 | Stenger | |
| 3,958,002 A | 5/1976 | Stenger | |
| 4,060,637 A | * 11/1977 | Stenger | |
| 4,140,769 A | 2/1979 | Schut | |
| 4,147,767 A | 4/1979 | Yapel | |
| 4,238,506 A | 12/1980 | Stach et al. | |
| 4,256,664 A | 3/1981 | Epstein | |
| 4,495,272 A | * 1/1985 | Yagihara | |
| 4,692,433 A | 9/1987 | Hostetler et al. | |
| 4,757,066 A | 7/1988 | Shiokari et al. | |
| 4,873,087 A | 10/1989 | Morishita et al. | |
| 4,895,725 A | 1/1990 | Kantor et al. | |
| 4,925,673 A | 5/1990 | Steiner | |
| 4,976,968 A | 12/1990 | Steiner | |
| 4,983,402 A | 1/1991 | Steiner | |
| 5,066,487 A | 11/1991 | Morelle et al. | |
| 5,352,461 A | 10/1994 | Feldstein et al. | |
| 5,401,516 A | 3/1995 | Milstein et al. | |
| 5,443,841 A | 8/1995 | Milstein et al. | |
| 5,447,728 A | 9/1995 | Milstein et al. | |
| 5,451,410 A | 9/1995 | Milstein et al. | |
| 5,455,335 A | 10/1995 | Kahane et al. | |
| 5,540,939 A | 7/1996 | Milstein et al. | |
| 5,541,155 A | 7/1996 | Leone-Bay et al. | |
| 5,578,323 A | 11/1996 | Milstein et al. | |
| 5,601,846 A | 2/1997 | Milstein et al. | |
| 5,629,020 A | 5/1997 | Leone-Bay et al. | |
| 5,643,957 A | 7/1997 | Leone-Bay et al. | |
| 5,650,386 A | 7/1997 | Leone-Bay et al. | |
| 5,667,806 A | 9/1997 | Kantor et al. | |
| 5,693,338 A | 12/1997 | Milstein et al. | |
| 5,705,529 A | 1/1998 | Matyus et al. | |
| 5,709,861 A | 1/1998 | Santiago et al. | |
| 5,714,167 A | 2/1998 | Milstein et al. | |
| 5,750,147 A | 5/1998 | Kantor et al. | |

(List continued on next page.)

FOREIGN PATENT DOCUMENTS

| | | | |
|---|---|---|---|
| DE | 1233877 | 2/1967 | |
| DE | 2142361 | 3/1972 | |
| EP | 0036145 | 9/1981 | |
| EP | 620218 | 10/1994 | |
| EP | 0796840 A3 | 1/1999 | |
| ES | 369853 | 7/1969 | |
| FR | 4446 | 11/1966 | |
| FR | 1489564 | 9/1967 | |
| FR | 1501151 | 11/1967 | |
| FR | 1543944 | 10/1968 | |
| FR | 0006425 M | 11/1968 | |
| JP | 48-37819 | 11/1973 | |
| JP | 02207063 | 8/1990 | |
| JP | 05239005 | 9/1993 | |
| WO | WO 9323374 | 11/1993 | |
| WO | WO 99/29705 | 6/1999 | ........... C07H/15/00 |

OTHER PUBLICATIONS

Chem Abst. 128:243929 (1998).*
Chem Abst 125:237590 (1996).*
Chem Abst 117:248148 (1992).*
Chem Abst. 120:216988 (1993).*
British Pharmacopoeia 1999, vol. 1, p. 974–975 (effective date Dec. 1, 1999).
Johansen et al., *Int'l. J. of Pharm.* 7 (1980) 119–127.
Davaran et al., Chemical Abstract No. 63362, *J. Controlled Release*, vol. 131, 58(3):279–287 (1999).
Chaturvedi, S.C. et.al. Indian Drugs Pharm Ind. 12(6), 43–4, 1977 Antimicrobial activity of N–(dimethylaminomehtyl-)salicylamide.
Chaturvedi, S.C. et.al. Indian J. Hosp. Pharm, 16(1). 20–1, 1979 Synthesis and antimicrobial activity of N–(dimethylaminomehtyl)salicylamide.
Singh, Guru Bachan, et al. Indian J. Pharm., 29(7), 206–08, 1967 Local anesthetic activity of Mannich bases of salicylamide and piperazine.
Bahekar, Rajesh H., Indian Drugs, 35(10), 648–52, 1998, "Synthesis and biological evaluation of indomethacin conjugates with salicylamide and its Mannich bases: a mutual prodrug approach".

(List continued on next page.)

Primary Examiner—Paul J. Killos
(74) Attorney, Agent, or Firm—Darby & Darby

(57) ABSTRACT

Compounds and compositions for the delivery of active agents are provided. Methods of administration and preparation are provided as well.

28 Claims, No Drawings

U.S. PATENT DOCUMENTS

| | | | |
|---|---|---|---|
| 5,766,633 | A | 6/1998 | Milstein et al. |
| 5,773,647 | A | 6/1998 | Leone-Bay et al. |
| RE35,862 | E | 7/1998 | Steiner et al. |
| 5,776,888 | A | 7/1998 | Leone-Bay et al. |
| 5,792,451 | A | 8/1998 | Sarubbi et al. |
| 5,804,688 | A | 9/1998 | Leone-Bay et al. |
| 5,811,127 | A | 9/1998 | Milstein et al. |
| 5,820,881 | A | 10/1998 | Milstein et al. |
| 5,824,345 | A | 10/1998 | Milstein et al. |
| 5,840,340 | A | 11/1998 | Milstein et al. |
| 5,863,944 | A | 1/1999 | Leone-Bay et al. |
| 5,866,536 | A | 2/1999 | Leone-Bay et al. |
| 5,876,710 | A | 3/1999 | Leone-Bay et al. |
| 5,879,681 | A | 3/1999 | Leone-Bay et al. |
| 5,935,601 | A | 8/1999 | Leone-Bay et al. |
| 5,939,381 | A | 8/1999 | Leone-Bay et al. |
| 5,955,503 | A | 9/1999 | Leone-Bay et al. |
| 5,958,457 | A | 9/1999 | Santiago et al. |
| 5,962,710 | A | 10/1999 | Gschneidner et al. |
| 5,965,121 | A | 10/1999 | Leone-Bay et al. |
| 5,972,387 | A | 10/1999 | Milstein et al. |
| 5,976,569 | A | 11/1999 | Milstein et al. |
| 5,989,539 | A | 11/1999 | Leone-Bay et al. |
| 5,990,166 | A | 11/1999 | Leone-Bay et al. |
| 6,001,347 | A | 12/1999 | Leone-Bay et al. |
| 6,051,258 | A | 4/2000 | Kantor |
| 6,051,561 | A | 4/2000 | Leone-Bay et al. |
| 6,060,513 | A | 5/2000 | Leone-Bay et al. |
| 6,071,510 | A | 6/2000 | Leone-Bay et al. |
| 6,071,538 | A | 6/2000 | Milstein et al. |
| 6,084,112 | A | 7/2000 | Ho et al. |
| 6,090,958 | A | 7/2000 | Milstein et al. |
| 6,099,856 | A | 8/2000 | Milstein et al. |
| 6,100,285 | A | 8/2000 | Kantor |
| 6,100,298 | A | 8/2000 | Leone-Bay et al. |
| 6,180,140 | B1 | 1/2001 | Leone-Bay et al. |
| 6,221,367 | B1 | 4/2001 | Milstein et al. |

OTHER PUBLICATIONS

Jaszay, Zsusza, et al. Synthesis 10, 745–7, 1989 Phase–transfer catalyzed synthesis of amides and esters of carboxylic acids.

Saettone, M.F.: Int. J. Cosmet. Sci. 8(1), 9–25, 1986 " Substantivuity of sunscreens: an appraisal of some quaternary ammonium sunscreens".

Koshy, K.T.; J. Pharm. Sci 58(5) 560–63, 1969 "Comparative stability of benzamide, salicylamide and some N–substituted derivatives".

Singh, Guru Bachan, et al. J. Indian Chem. Soc. 44(12), 1009–13, 1967 N–Mannich bases of 3,5–dibromosalicylamide and 3,5–dichlorosalicylamide.

Tramposch, Kenneth M. Appl. Nucl. Radiochem 205–13, 1982 "Radioiodine–labeled amines as brain imaging agents".

Baldazzi, Claudia et al. Arzneim.–Forsch. 46(9), 911–918, 1996 A new Series of 6–chloro-2, 3–dihydro–4(1H)–quinazolinone derivatives as antiemetic and gastrointenstinal motility enhancing agents.

Minasyan, S. A et al..; Iarm. Khim. Zh. 39(3) 169–74, 1986 Phenolic acid derivatives XXIII Synthesis of (dialkylamino)alkylamides of phenolic acids.

Mohammed, A. et al. Nucl. Med. Biol, 24(5) 373–380 1997 "Radioiodinated N–(alkylaminoalkyl)–substituted 4–mehtoxy–, 4–hydroxy–, and 4 aminobenzamides: biological investigations for the improvemtn of melanoma–imaging agents".

Iyengar, R.R et al..; Indian J. Chem. Sect. A, 28A(6), 445–51, 1989 Thermodynamic vies of hydrophobic association of side chains of aromatic amino acids.

Knabe, Joachim et al. Arch. Pharm 313(6), 538–43, 1980 Racemic and optically active hydantoins from disubstituted cyanoacetic acids'.

Schoellkopf, Ulrich, et al. Liebigs Ann. Chem (12), 2150–63, 1986 Asymetric syntheses via hetrocyclic intermediaries.

Wu, Guang et al. J., Imaging Sci. 39(3), 253–7, 1995 "Crystal structures of blue–sensitizing dyes".

CAS Registry No. 46803–81–0.

Nakatsuka, Haruo; et al. Radioisotopes, 15(3), 147–57 1966, Distribution of colloidal radioactive gold, chromic phosphate, and lutetium chloride administered in normal and ascites tumor–bearing mice.

Phillips Barrie Maurice, J. Pharm Sci. 58(11) 1414–16, 1969 " Ring opening of cyclic salicylamides".

Thominet, Michel Leon et al. Otkrytiya Izobret. Prom Obraztsy, Tovarnye Znaki (4), 216–17 1979 Benzamide derivatives and their salts.

Venuti, Michael C. et al. J. Med Chem 30(2), 303–18 1987 " Inhibitors of cyclic AMP phophodiesterase".

Kumar, Yatendra, et al. Eur. J. Med. Chem.–Chim. Ther. 21(1) 1–3, 1986 "Synthesis and neuroleptic activity of substituted benazmides related to metoclopramide".

Palagiano, F. et al.: "Synthesis, stability and anticonvulsant activity of two new GABA prodrugs," *Pharamazic*, 52 (4): 272–276 (1997), XP–001084051.

Yalcin, I. et al.: "Synthesis and Microbiological Activity of Some Novel N–(2–Hydroxyl–5–Substitutedphenyl)Benzacetamides, Phenoxyacetamides and Thiophenoxycetamides as the Possible Metabolites of Antimicrobial Active Benzoxazoles," *Il Farmaco*, 52 (11), 685–689 (1997).

Lohr, L., J. Phys. Chem., 93(12):4697–4699 (1989).

Ostrovskaya et al., Field Analytical Chemistry and Technology, 4(2–3):147–153 (2000).

* cited by examiner

COMPOUNDS AND COMPOSITIONS FOR DELIVERING ACTIVE AGENTS

This is a continuation of International Application Serial No. PCT/US00/04830, filed Feb. 25, 2000, and claims the benefit under 35 U.S.C. §119 of U.S. Provisional Application Serial No. 60/121,850 filed Feb. 26, 1999, the entire disclosures of which are hereby incorporated by reference.

FIELD OF THE INVENTION

The present invention relates to compounds for delivering active agents, such as biologically or chemically active agents, to a target. These compounds are well suited for forming non-covalent mixtures with active agents for oral or intracolonic or other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, proteinoid microspheres have been used to deliver pharmaceuticals. For example, see U.S. Pat. No. 5,401,516, U.S. Pat. No. 5,443,841 and U.S. RE35,862. In addition, certain modified amino acids have been used to deliver pharmaceuticals. See, e.g., U.S. Pat. No. 5,629,020; U.S. Pat. No. 5,643,957; U.S. Pat. No. 5,766,633; U.S. Pat. No. 5,776,888; and U.S. Pat. No. 5,866,536.

However, there is still a need for simple, inexpensive delivery systems which are easily prepared and which can deliver a broad range of active agents by various routes.

SUMMARY OF THE INVENTION

Compounds and compositions that are useful in the delivery of active agents are provided. The present invention encompasses compounds having the following formula, or salts thereof, or mixtures thereof.

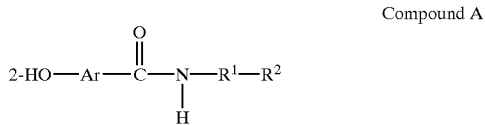

Compound A wherein
Ar is phenyl or naphthyl;
Ar is optionally substituted with $C_1$–$C_4$ alkyl, $C_1$–$C_4$ alkoxy, $C_2$–$C_4$ alkenyl, $C_2$–$C_4$ alkynyl, aryl, aryloxy, a heterocyclic ring, $C_5$–$C_7$ carbocyclic ring, halogen, —OH, —SH, —$CO_2R^6$, —$NR^7R^8$ or —$N^+R^7R^8R^9Y$;

(a) $R^1$ is $C_1$–$C_{16}$ alkylene, $C_2$–$C_{16}$ alkenylene, $C_2$–$C_{16}$ alkynylene, $C_6$–$Cl_{16}$ arylene, ($C_1$–$C_{16}$ alkyl)arylene, or aryl($C_1$–$C_{16}$ alkylene);

$R^2$ is —$NR^3R^4$ or —$N^+R^3R^4$ or —$N^+R^3R^4R^5Y$;

$R^3$ and $R^4$ are independently hydrogen; oxygen; hydroxy; substituted or unsubstituted $C_1$–$C_{16}$ alkyl; substituted or unsubstituted $C_2$–$C_{16}$ alkenyl; substituted or unsubstituted $C_2$–$C_6$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; or substituted or unsubstituted aryloxycarbonyl; and $R^5$ are independently hydrogen; substituted or unsubstituted $C_1$–$C_{16}$ alkyl; substituted or unsubstituted $C_2$–$C_{16}$ alkenyl; substituted or unsubstituted $C_2$–$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; or substituted or unsubstituted aryloxycarbonyl;

(b) $R^1$ $R^2$, and $R^5$ are as defined above; and $R^3$ and $R^4$ are combined to form a 5, 6, or 7-membered heterocyclic ring or 5, 6 or 7-membered heterocyclic ring substituted with $C_1$–$C_6$ alkyl, $C_1$–$C_6$ alkoxy, aryl, aryloxy, oxo group, or carbocyclic ring; or (c) $R^2$ and $R^5$ are as defined above;

$R^1$ and $R^3$ are combined to form a 5, 6, or 7-membered heterocyclic ring; or 5, 6, or 7-membered heterocyclic ring substituted with $C_1$–$C_6$ alkyl, alkoxy, aryl, aryloxy, oxo group or carbocyclic ring; and $R^4$ is hydrogen; oxygen; hydroxy; substituted or unsubstituted $C_1$–$C_{16}$ alkyl; substituted or unsubstituted $C_2$–$C_{16}$ alkenyl; substituted or unsubstituted $C_2$–$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; or substituted or unsubstituted aryloxycarbonyl;

$R^6$ is hydrogen; $C_1$–$C_4$ alkyl; $C_1$–$C_4$ alkyl substituted halogen or —OH; $C_2$–$C_4$ alkenyl; or $C_2$–$C_4$ alkenyl substituted with halogen or —OH;

$R^7$, $R^8$ and $R^9$ are independently hydrogen; oxygen; $C_1$–$C_4$ alkyl; $C_1$–$C_4$ alkyl substituted with halogen or —OH; $C_2$–$C_4$ alkenyl; or $C_2$–$C_4$ alkenyl substituted with halogen or —OH; and Y is halogen, hydroxide, sulfate, nitrate, phosphate, alkoxy, perchlorate, tetrafluoroborate, or carboxylate. An example of a suitable carboxylate includes, but is not limited to acetate.

Preferably, at least one of $R^3$ and $R^4$ is not hydrogen.

In a preferred embodiment, Ar is phenyl optionally substituted with methyl; methoxy; hydroxy; or halogen. More preferably, Ar is unsubstituted phenyl or phenyl substituted with chlorine, more preferably at the 5 position.

According to another embodiment, $R^1$ is a $C_1$–$C_{12}$ substituted or unsubstituted alkylene. Preferably, $R^1$ is a $C_3$–$C_8$ unsubstituted alkylene. More preferably, $R^1$ is a $C_6$ unsubstituted alkylene.

According to another embodiment, $R^2$ is —$NR^3R^4$; and (i) $R^3$ is phenyl or cyclohexyl and $R^4$ is hydrogen; (ii) $R^3$ and $R^4$ are both methyl; or (iii) $R^3$ and $R^4$ are combined to form a 5- or 6-membered heterocyclic ring containing nitrogen, such as preferably pyrrolidinone, morpholine and imidazole.

According to yet another embodiment, $R^2$ is —$N^+R^3R^4R^5$ Y.

According to a preferred embodiment, the compound has the formula:

Compound B wherein $R^{11}$, $R^{12}$, $R^{13}$ and $R^{14}$ are independently hydrogen, —OH, halogen, $C_1$–$C_4$ alkyl, $C_1$–$C_4$ haloalkyl, $C_1$–$C_4$ alkoxy, or $C_1$–$C_4$ haloalkoxy;

$R^{15}$ is substituted or unsubstituted $C_1$–$C_{12}$ alkylene;

$R^{16}$ and $R^{17}$ are independently hydrogen, $C_1$–$C_4$ alkyl, $C_5$–$C_7$ cycloalkyl, or phenyl; or $R^{16}$ and $R^{17}$ are combined to form a 5 or 6 atom heterocyclic ring; and salts thereof. Preferably, $R^{11}$, $R^{12}$, $R^{13}$ and $R^{14}$ are independently hydrogen; —OH; or halogen, more preferably chlorine. Preferably, $R^{15}$ is unsubstituted $C_3$–$C_8$ alkylene.

According to one embodiment, $R^{16}$ and $R^{17}$ are methyl. According to another embodiment, $R^{16}$ and $R^{17}$ are combined to form a pyrrolidinone, morpholine, or imidazole ring, Preferred compounds of the present invention include, but are not limited to:

Compound 1

Compound 2

Compound 3

Compound 4

Compound 5

Compound 6

Compound 7

Compound 8

-continued

Compound 9

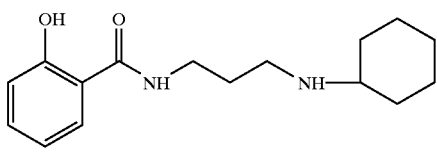

Compound 10

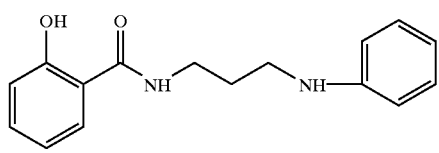

Compound 11

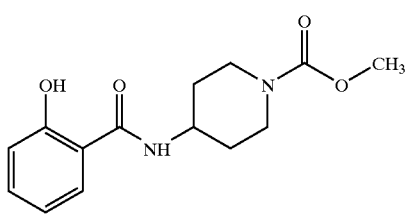

Compound 12

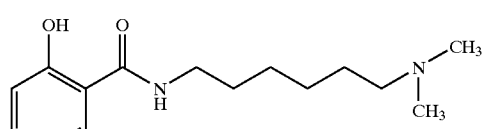

Compound 13

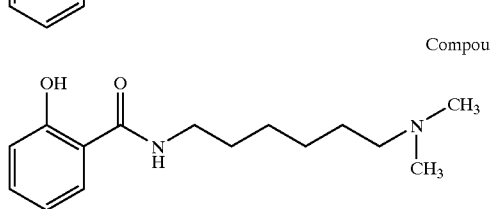

The compositions of the present invention comprise at least one active agent, preferably a biologically or chemically active agent, and at least one of the compounds, or salts thereof, of the present invention. Methods for the preparation and administration of such compositions are also provided.

Also provided are dosage unit forms comprising the compositions. The dosing vehicle can be a solid (such as a tablet, powder, or capsule) or a liquid.

Methods for administering a biologically active agent to an animal in need of the agent, especially by the oral or intracolonic routes, with the compositions of the present invention, are also provided.

DETAILED DESCRIPTION OF THE INVENTION

The term "substituted" as used herein includes, but is not limited to, the following substituents: halogen and —OH.

All carbon containing substituents described in the formulae for compounds A and B, such as alkyl, alkenyl, alkynyl moieties, may be linear or branched.

The compounds may be in the form of the amine salts. Salts include, but are not limited to, organic and inorganic salts, for example, ammonium salts and hydrochloride salts.

In general, the amine compounds of the present invention, i.e., where $R^2$ is —$NR^3R^4$, may be prepared by reacting the appropriate O-acetyl salicyloyl chloride with the appropriate amine in the presence of a base, such as triethylamine. To obtain the corresponding quaternary ammonium salt where $R^2$ is —$NHR^3R^4$, the amine compound is reacted with hydrochloric acid and preferably an excess of hydrochloric acid. To obtain the corresponding quaternary ammonium salt where $R^2$ is —$NR^3R^4R^5$ (where $R^3$, $R^4$, and $R^5$ are not hydrogen), the amine moiety of the amine compound is alkylated by methods known in the art.

The compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0–500 mM sodium chloride gradient is employed.

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of mucopolysaccharides; carbohydrates; lipids; other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone-releasing hormones; interferons, including a, b and (; interleukin-1; interleukin-2; insulin, including porcine, bovine, human, and human recombinant, optionally having counter ions including sodium, zinc, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; vitamins; analogs, fragments, mimetics or polyethylene glycol (PEG)-modified derivatives of these compounds; or any combination thereof.

Delivery Systems

The compositions of the present invention comprise a delivery agent and one or more active agents. In one embodiment, one or more of the delivery agent compounds, or salts of these compounds, may be used as a delivery agent by mixing with the active agent prior to administration.

The administration compositions may be in the form of a liquid. The solution medium may be water (for example, for salmon calicitonin, parathyroid hormone, and erthyropoietin), 25% aqueous propylene glycol (for example, for heparin) and phosphate buffer (for example, for rhGH). Other dosing vehicles include polyethylene glycols, sorbitol, maltitol, and sucrose. Dosing solutions may be prepared by mixing a solution of the delivery agent compound with a solution of the active agent, just prior to administration. Alternately, a solution of the delivery agent (or active agent) may be mixed with the solid form of the active agent (or delivery agent). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or powder. Solid dosage forms may be prepared by mixing the solid form of the compound with the solid form of the active agent. Alternatively, a solid may be obtained from a solution of compound and active agent by methods known in the art, such as freeze drying, precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions may deliver active agents more efficiently than prior compositions, lower amounts of biologically or chemically active agents than those used in prior dosage unit forms or delivery systems can be administered to the subject, while still achieving the same blood levels and/or therapeutic effects.

The presently disclosed compounds deliver biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

EXAMPLE 1

Preparation of Compound 1

To a 250 ml three neck round-bottomed flask equipped with a magnetic stirrer and a reflux condenser was placed 7.11 g (50 mmol) of 1-(3-aminopropyl)-2-pyrrolidinone in 70 ml of dichloromethane. Chlorotrimethylsilane (6.34 ml, 50 mmol) was added in one portion. The mixture was refluxed for about 1 hour. The reaction was cooled to approximately 5° C. Triethylamine (10.45 ml, 75 mmol) was added dropwise, followed by the addition dropwise of a solution of 9.93 g (50 mmol) of o-acetylsalicyloyl chloride in 20 ml of dichloromethane. After the addition had been completed, the mixture was allowed to warm to room temperature and was stirred for an additional hour. The mixture was concentrated in vacuo to an oil. An ice cold solution of 2 M sodium hydroxide (100 ml, 200 mmol) was added and the mixture was stirred for about 2 hours. The basic solution was acidified with a 10% solution of hydrochloric acid. The organic product was extracted with ethyl acetate. The organic phase was washed with water until neutrality, dried and concentrated in vacuo to afford a residue which was purified by flash column chromatograph to yield 7.9 g (61%) of a white solid. Spectroscopic data and combustion analysis indicated the assigned structure.

Compound 2 was also prepared by this method. Compounds 3–11 may also be prepared by this method.

Preparation of Compound 12

A slurry of 18.02 g (110 mmol) of carsalam, 18.0 ml (15.84 g, 109 mmol) of 6-dimethylamino-1-hexanol, 29.12 g (111 mmol) of triphenylphosphine, and 150 ml of tetrahydrofuran was treated with a solution of 21.8 ml (22.39 g, 111 mmol) of disopropyl azodicarboxylate and 40 ml of tetrahydrofuran, added dropwise over 20 minutes, causing the temperature of the slurry to rise to about 67° C. The reaction mixture was allowed to cool back to about 25° C. and stir for about 20 hours. The solution was treated with 150 ml (300 mmol) of aqueous 2 N sodium hydroxide and warmed to about 60° C. for about 90 minutes. The reaction mixture was washed with ethyl acetate (2×60 ml). The aqueous phase was acidified with 4% aqueous hydrochloric acid to a pH slightly less than about 0 and washed with ethyl acetate (2×60 ml). The pH of the aqueous phase was raised to about 4.5 with 50% aqueous potassium carbonate and washed with ethyl acetate (2×60 ml). The aqueous phase was treated with solid sodium bicarbonate and extracted with ethyl acetate (14×60 ml). The combined 14 ethyl acetate extracts were dried over sodium sulfate and concentrated to a viscous liquid. The liquid was taken up into a minimum amount of ethyl acetate, diluted with 100 ml of hexanes and treated in an ice bath with 150 ml of hexanes, causing a white solid to develop. A total of 13.65 g of N-(6-dimethylaminohexyl)salicylamide was isolated by filtration.

Preparation of Compound 13

A slurry of 5.79 g (29.3 mmol) of 6-chlorocarsalam, 4.80 ml (4.22 g, 29.1 mmol) of 6-dimethylamino-1-hexanol, 7.71 g (29.4 mmol) of triphenylphosphine, and 50 ml of tetrahydrofuran was treated with a solution of 5.8 ml (5.96 g, 29.5 mmol) of disopropyl azodicarboxylate and 20 ml of tetrahydrofuran, added dropwise over 20 minutes, causing the temperature of the slurry to rise to about 67° C. The reaction mixture was allowed to cool back to about 25° C. and stir for about 20 hours. The solution was treated with 50 ml (100 mmol) of aqueous 2 N sodium hydroxide and warmed to about 60° C. for about 120 minutes. The reaction mixture was washed with ethyl acetate (2×40 ml). The aqueous phase was acidified with 4% aqueous hydrochloric acid to a pH of about 1 and washed with ethyl acetate (2×40 ml). The pH of the aqueous phase was raised to about 5.5 with 50% aqueous potassium carbonate, causing a white solid to develop. A total of 5.25 g of N-(6-dimethylaminohexyl)-5-chlorosalicylamide was isolated by filtration.

EXAMPLE 2

Oral Delivery of Salmon Calcitonin (sCT)

Oral dosing (PO) compositions of delivery agent compound and salmon calcitonin (sCT) in water were prepared. Typically, 450 mg of compound was added to 2.0 ml of water. Either the sodium salt of the compound was used or the free acid was converted to the sodium salt by stirring the resultant solution and adding one equivalent of sodium hydroxide (1.0 N) and diluting with water. The solution was vortexed, then heated (about 37° C.) and sonicated. The pH was adjusted to about 7 (6.5 to 8.5) with sodium hydroxide or hydrochloric acid. 90 mg sCT from a stock solution was added to the solution. Water was then added to bring the total volume to about 3.0 ml (varying depending on the solubility of the delivery agent compound) and vortexed. The final delivery agent compound dose, sCT dose, and volume dose amounts are listed below in Table 1.

The typical dosing and sampling protocols were as follows. Male Sprague-Dawley rats weighing between 200–250 g were fasted for 24 hours and administered ketamine (44 mg/kg) and chlorpromazine (1.5 mg/kg) 15 minutes prior to dosing. A dosing group of five rats was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically before administration and 10, 20, 30, 60 and 90 minutes after administration. Serum sCT was determined by testing with an EIA kit (Kit # EIAS-6003 from Peninsula Laboratories, Inc. of San Carlos, Calif.). Numbers were adjusted according to baseline values obtained prior to administration. The results from the five rats in each dosing group were averaged for each time point. The maximum is reported below in Table 1.

TABLE 1

Oral Delivery of Salmon Calcitonin (sCT)

| Compound | Volume Dose (ml/kg) | Compound Dose (mg/kg) | sCT Dose (mg/kg) | Mean Peak Serum Sct (pg/ml ± SD)(SE) |
|---|---|---|---|---|
| 12 | 1 | 150 | 30 | 764 ± 443(167) |

EXAMPLE 4

Oral Delivery of Low Molecular Weight Heparin (LMWH)

Intracolonic (IC) compositions containing a delivery agent compound and low molecular weight heparin (LMWH) in 25% aqueous propylene glycol were prepared. Either the sodium salt of the compound was used or the free acid was converted to the sodium salt with one equivalent of sodium hydroxide. Typically, delivery agent compound and LMWH (91 IU/mg, average molecular weight about 5,000) were mixed by vortex as dry powders. This dry mixture was dissolved in 25% v/v aqueous propylene glycol, vortexed and placed in a sonicator (37° C.). The pH was adjusted to about 7 (6.5–8.5) with 2 N aqueous sodium hydroxide. The dosing solution was sonicated to produce a clear solution. The final volume was adjusted to 3.0 ml. The final delivery agent compound dose, LMWH dose, and volume dose amounts are listed below in Table 2.

The typical dosing and sampling protocols were as follows. Male Sprague-Dawley rats weighing between 275–350 g were fasted for 24 hours and were anesthetized with ketamine hydrochloride (88 mg/kg) intramuscularly immediately prior to dosing. A dosing group of five rats was administered one of the dosing solutions. For intracolonic (IC) dosing, a 7.5 cm, 8 fr Rusch catheter was adapted to a 1 ml syringe with a pipette tip. The dosing catheter was inserted into the colon through the anus until the tube was no longer visible. The dosing solution was expressed slowly into the colon by pressing the syringe plunger. Citrated blood samples were collected by cardiac puncture following the administration of ketamine (88 mg/kg), typically 0.5, 1.0, 2.0, 3.0 and 4.0 hours after administration. LMWH activity was determined using the anti-Factor Xa assay CHROMOSTRATE® heparin anti-$X_a$ assay, available from Organon Teknika Corporation of Durham, N.C. Baseline values are about zero IU/ml. Results from the five rats in each group were averaged for each time point. The mean peak plasma heparin concentration is reported below in Table 2.

TABLE 2

Intracolonic Delivery of LMWH

| Compound | Method of Administration | Volume Dose (ml/kg) | Compound Dose (mg/kg) | LMWH Dose (IU/kg) | Mean Peak Plasma Heparin Concentration (IU/ml) ± Standard Deviation |
|---|---|---|---|---|---|
| 12 | IC | 1 | 50 | 750 | 0.13 ± 0.05 |

EXAMPLE 5

Recombinant Human Growth Hormone (rhGH)

Oral gavage (PO) dosing solutions of delivery agent compound and rhGH in phosphate buffer were prepared. A solution of the compound was made either with the sodium salt of the compound or by converting the free acid to its sodium salt. Typically, a solution of the compound was prepared in phosphate buffer and stirred, adding one equivalent of sodium hydroxide (1.0 N) when making the sodium salt. The final dosing solutions were prepared by mixing the compound solution with an rhGH stock solution (15 mg rhGH/ml made by mixing as powders 15 mg rhGH, 75 mg D-mannitol, 15 mg glycine and 3.39 mg dibasic sodium phosphate, then diluting with 2% glycerol) and diluting to the desired volume (usually 3.0 ml). The compounds and rhGH dose amounts are listed below in Table 3.

The typical dosing and sampling protocols were as follows. Male Sprague-Dawley rats weighing between 200–250g were fasted for 24 hours and administered ketarnine (44 mg/kg) and chlorpromazine (1.5 mg/kg) 15 minutes prior to dosing. A dosing group of five rats was administered one of the dosing solutions. For oral gavage (PO), an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger.

Blood samples were collected serially from the tail artery, typically at time =15, 30, and 45 minutes. The five samples from each time period were pooled. Serum rHGH concentrations were quantified by an rHGH immunoassay test kit (Kit # K1F4015 from Genzyme Corporation Inc., Cambridge, Mass.). Previous studies indicated baseline values of about zero.

The maximum concentration for each group and the area under the curve (AUC) are reported below in Table 3.

TABLE 3

Oral Delivery of rhGH in Rats

| Compound | Method of Administration | Volume dose (ml/kg) | Compound Dose (mg/kg) | rhGH Dose (mg/kg) | Mean Peak Serum [rhGH] (ng/ml) | AUC |
|---|---|---|---|---|---|---|
| 12 | PO | 1 | 200 | 3 | 51.76 | 1044.75 |

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:
1. A compound selected from

Compound 1

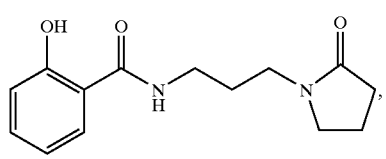

Compound 4

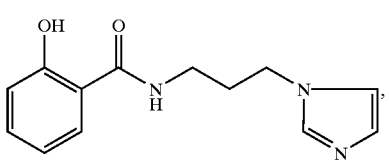

Compound 6

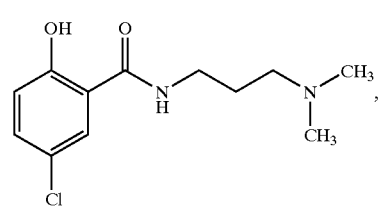

Compound 7

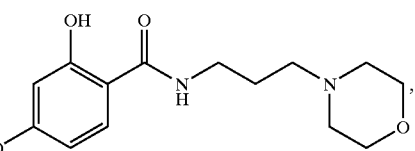

Compound 8

Compound 9

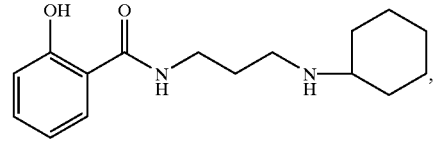

-continued
Compound 10
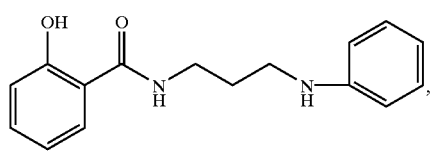
Compound 11
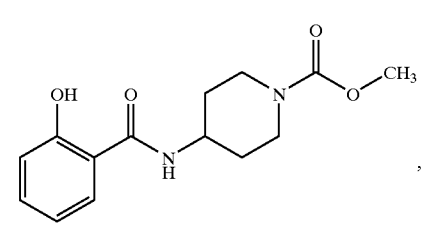
Compound 12
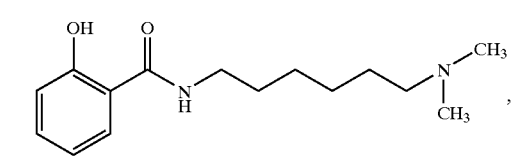
Compound 13
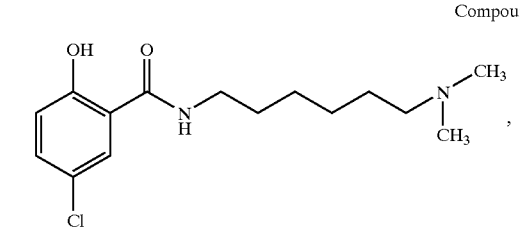
and salts thereof.
2. A composition comprising:
   (A) an active agent; and
   (B) at least one compound selected from
Compound 1
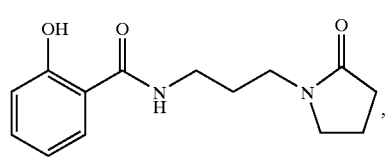
Compound 2
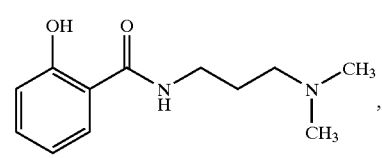
Compound 3
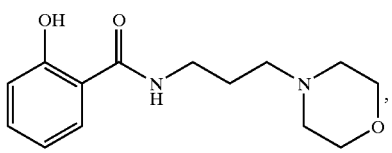
Compound 4
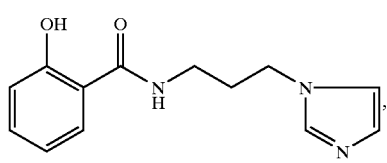
-continued
Compound 5
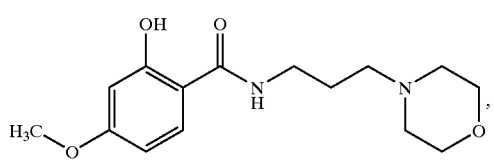
Compound 6
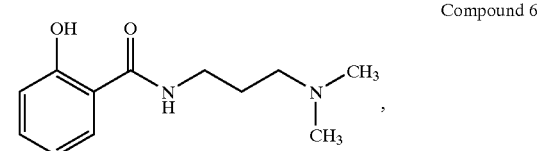
Compound 7
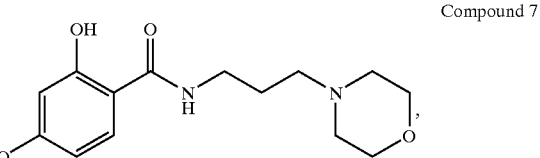
Compound 8
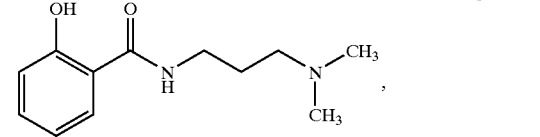
Compound 9
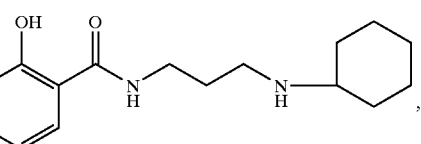
Compound 10
Compound 11
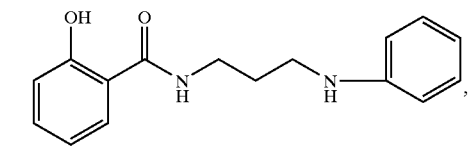
Compound 12
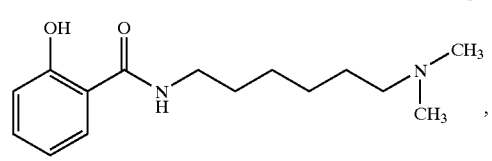

-continued

Compound 13

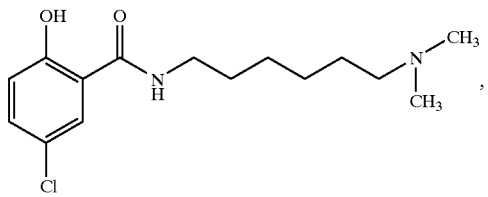

and salts thereof.

3. The composition of claim 2, wherein the active agent is selected from the group consisting of a biologically active agent, a chemically active agent, and a combination thereof.

4. The composition of claim 3, wherein the biologically active agent comprises at least one protein, polypeptide, peptide, hormone, polysaccharide, mucopolysaccharide, carbohydrate, or lipid.

5. The composition of claim 3, wherein the biologically active agent is selected from the group consisting of: growth hormones, human growth hormones recombinant human growth hormones (rhGH), bovine growth hormones, porcine growth hormones, growth hormone releasing factor, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim. postaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

6. The composition of claim 5, wherein the biologically active agent comprises insulin, heparin, calcitonin, parathyroid hormone, erythropoietin, growth hormones or combinations thereof.

7. The composition of claim 5, wherein the biologically active agent comprises recombinant human growth hormone.

8. The composition of claim 5, wherein the biologically active agent comprises parathyroid hormone.

9. The composition of claim 5, wherein the biologically active agent comprises insulin.

10. The composition of claim 5, wherein the biologically active agent comprises heparin.

11. The composition of claim 5, wherein the biologically active agent comprises calcitonin.

12. The composition of claim 5, wherein the biologically active agent comprises interferon.

13. The composition of claim 5, wherein the biologically active agent comprises cromolyn.

14. A dosage unit form comprising:
(A) the composition of claim 2; and
(B) (a) an excipient
  (b) a dilutent
  (c) a disintegrant,
  (d) a lubricant,
  (e) a plasticizer,
  (f) a colorant,
  (g) a dosing vehicle, or
  (h) any combination thereof.

15. The dosage unit form of claim 14, wherein the active agent is selected from the group consisting of a biologically active agent, a chemically active agent, and a combination thereof.

16. The dosage unit form of claim 15, wherein the biologically active agent comprises at least one protein, polypeptide, peptide, hormone, polysaccharide, mucopolysaccharide, carbohydrate, or lipid.

17. The dosage unit form of claim 16, wherein the biologically active agent is selected from the group consisting of:
  growth hormones, human growth hormones (hGH), recombinant human growth hormones (rhGH), bovine growth hormones, porcine growth hormones, growth hormone releasing hormones, growth hormone releasing factor, interferons, α-interferon, β-interferon, γ-interferon, interleukin-1, interleukin-2, insulin, porcine insulin, bovine insulin, human insulin, human recombinant insulin, insulin-like growth factor, insulin-like growth factor-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin, atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim. postaglandins, cyclosporin, vasopressin, cromolyn sodium, sodium chromoglycate, disodium chromoglycate, vancomycin, desferrioxamine, parathyroid hormone, fragments of PTH, antimicrobials, anti-fungal agents, vitamins; analogs, fragments, mimetics and polyethylene glycol-modified derivatives of these compounds; and any combination thereof.

18. The dosage unit form of claim 15, wherein the biologically active agent comprises insulin, heparin, calcitonin, parathyroid hormone, erythropoietin, human growth hormones or combinations thereof.

19. The dosage unit form of claim 15, wherein the active agent comprises recombinant human growth hormone.

20. The dosage unit form of claim 15, wherein the active agent comprises parathyroid hormone.

21. The dosage unit form of claim 15, wherein the active agent comprises insulin.

22. The dosage unit form of claim 15, wherein the active agent comprises heparin.

23. The dosage unit form of claim 15, wherein the active agent comprises calcitonin.

24. The dosage unit form of claim 15, wherein the active agent comprises interferon.

25. The dosage unit form of claim 15, wherein the dosage unit form comprises a dosing vehicle comprising a tablet, a capsule, a powder, or a liquid.

26. The dosage unit form of claim 15, wherein the dosing vehicle is liquid selected from the group consisting or water, 1,2-propane diol, ethanol, and any combination.

27. A method for administering a biologically-active agent to an animal in need of the agent, the method comprising administering orally to the animal the composition of claim 3.

28. A method for preparing a composition comprising mixing:

(A) at least one active agent;

(B) the compound of claim 1, and (C) optionally, a dosing vehicle.

* * * * *